United States Patent [19]

Dowle et al.

[11] Patent Number: 4,816,470

[45] Date of Patent: Mar. 28, 1989

[54] HETEROCYCLIC COMPOUNDS

[75] Inventors: Michael D. Dowle; Ian H. Coates, both of Hertford, England

[73] Assignee: Glaxo Group Limited

[21] Appl. No.: 789,831

[22] Filed: Nov. 15, 1985

Related U.S. Application Data

[63] Continuation of Ser. No. 680,532, Dec. 11, 1984, which is a continuation of Ser. No. 501,999, Jun. 7, 1983, abandoned.

[30] Foreign Application Priority Data

Jun. 7, 1982 [GB] United Kingdom ................ 8216526

[51] Int. Cl.⁴ .................... A61K 31/40; C07D 209/16
[52] U.S. Cl. .................................. 514/415; 548/504; 548/505
[58] Field of Search ................ 548/504, 505; 514/415

[56] References Cited

U.S. PATENT DOCUMENTS 4,636,521 1/1987 Coates et al. ............... 548/504
4,650,810 3/1987 Bays et al. .................. 548/504
4,672,067 6/1987 Coates et al. ............... 548/504

Primary Examiner—Mary E. Ceperley
Attorney, Agent, or Firm—Bacon & Thomas

[57] ABSTRACT

Indole derivatives of the general formula (I) are disclosed:

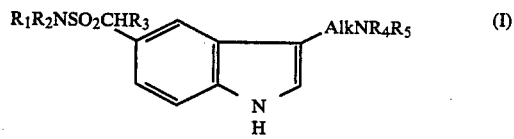

where $R_1$ is H or an alkyl or alkenyl group,
$R_2$ is H, or an alkyl, alkenyl, aryl, aralkyl or cycloalkyl group;
$R_3$ is H or an alkyl group;
$R_4$ and $R_5$ are independently H or an alkyl or propenyl group or together form an aralkylidene group; and
Alk is an optionally substituted alkylene chain; and their physiologically acceptable salts and solutes.

These compounds are potentially useful for the treatment of migraine and may be formulated as pharmaceutical compositions in conventional manner.

Various methods for the production of the compounds are disclosed including a Fischer-indole cyclization process.

18 Claims, No Drawings

HETEROCYCLIC COMPOUNDS

This application is a continuation of application Ser. No. 680,532 filed Dec. 11, 1984 now abandoned, which is a continuation of Ser. No. 501,999 filed June 7, 1983 now abandoned.

This invention relates to heterocyclic compounds, to processes for their preparation, to pharmaceutical compositions containing them and to their medical use.

The present invention provides an indole of the general formula (I):

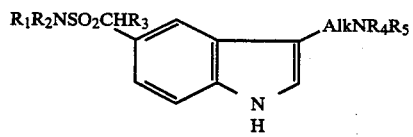

wherein
$R_1$ represents a hydrogen atom or a $C_{1-6}$ alkyl or $C_{3-6}$ alkenyl group;
$R_2$ represents a hydrogen atom or a $C_{1-3}$ alkyl, $C_{3-6}$ alkenyl, aryl, ar($C_{1-4}$)alkyl or $C_{5-7}$ cycloalkyl group;
$R_3$ represents a hydrogen atom or a $C_{1-3}$ alkyl group;
$R_4$ and $R_5$, which may be the same or different, each represents a hydrogen atom or a $C_{1-3}$ alkyl or propenyl group or $R_4$ and $R_5$ together form an aralkylidene group; and
Alk represents an alkylene chain containing two or three carbon atoms which may be unsubstituted or substituted by not more than two $C_{1-3}$ alkyl groups, and physiologically acceptable salts and solvates (e.g. hydrates) thereof.

All optical isomers of compounds of general formula (I) and their mixtures including the racemic mixtures thereof, are embraced by the invention.

Referring to the general formula (I), the alkyl groups in the general formula (I) may be straight chain or branched chain alkyl groups containing 1 to 3 carbon atoms, or in the case of $R_1$, 1 to 6, preferably 1 to 3, carbon atoms. Examples of an alkyl group include methyl, ethyl, propyl and isopropyl groups. The alkenyl groups preferably contain 3 or 4 carbon atoms, examples of which include propenyl and butenyl groups. The cycloalkyl groups preferably contain 5 or 6 carbon atoms and examples include cyclopentyl and cyclohexyl groups. The term aryl, used as such or in the term aralkyl, preferably means phenyl. The alkyl moieties of the aralkyl groups preferably contain 1 or 2 carbon atoms. Examples of an aralkyl group include benzyl and phenethyl groups. The aralkylidene group is preferably and aryl methylidene group such as benzylidene.

Suitable physiologically acceptable salts of the indoles of general formula (I) include acid addition salts formed with organic or inorganic acids for example hydrochlorides, hydrobromides, sulphates, fumarates, maleates and succinates. Other salts may be useful in the preparation of the compounds of general formula (I) e.g. creatinine sulphate adducts.

It is generally believed that the pain of migraine is of vascular origin and caused by excessive dilation of branches of the common carotid arterial bed (J. W. Lance, Mechanisms and Management of Migraine, Butterworths, p 113-152 (1973)) and a variety of vasoconstrictor agents have been shown to alleviate the headache. The compounds of the invention mimic methysergide in contracting the dog isolated saphenous vein strip (E. Apperley et al., Br. J. Pharmacol., 1980, 68, 215-224). Methysergide and ergotamine are known to be useful in the treatment of migraine and produce an increase in carotid vascular resistance in the anaesthetised dog; it has been suggested (P. R. Saxena., Eur. J. Pharmacol, 1974, 27, 99-105 and P. R. Saxena and G. M. De Vlaam-Schluter, Headache, 142, 1974) that this is the basis of their efficacy. Those compounds which we have tested selectively constrict the carotid arterial bed of the anaesthetised dog and the compounds according to the invention are thus potentially useful for the treatment of migraine.

Accordingly the invention also provides a pharmaceutical composition adapted for use in medicine which comprises at least one compound of formula (I), a physiologically acceptable salt or solvate (e.g. hydrate) thereof and formulated for administration by any convenient route. Such compositions may be formulated in conventional manner using one or more pharmaceutically acceptable carriers or excipients.

Thus the compounds according to the invention may be formulated for oral, buccal, parenteral or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The compounds of the invention may be formulated for parenteral administration by injection, including using conventional catheterisation techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for oral, parenteral, rectal or buccal administration to man for the treatment of migraine is 0.1 to 100 mg of the active ingredient per dose which could be administered, for example 1 to 4 times per day.

Aerosol formulations are preferably arranged so that each metered dose or "puff" of aerosol contains 20 μg–1000 μg of a compound of the invention. The overall daily dose with an aerosol will be within the range 100 μg–10 mg. Administration may be several times daily, for example 2, 3, 4 or 8 times, giving for example 1, 2 or 3 doses each time. The overall daily dose and the metered dose delivered by capsules and cartridges in an inhaler or insufflator could be double those with aerosol formulations.

A preferred class of compounds represented by the general formula (I) is that in which $R_1$ represents a hydrogen atom or a $C_{1-6}$ alkyl group and $R_2$ represents a hydrogen atom or a $C_{1-3}$ alkyl, $C_{3-6}$ alkenyl or ar($C_{1-4}$)alkyl group.

Another preferred class of compounds represented by the general formula (I) is that in which $R_3$, represents a hydrogen atom.

A further preferred class of compounds is that wherein, in the general formula (I), $R_4$ and $R_5$, which may be the same or different, each represents a hydrogen atom or a $C_{1-3}$ alkyl group, for example, a methyl group.

A preferred class of compounds falling within the scope of general formula (I) is that wherein $R_1$ represents a hydrogen atom or a $C_{1-3}$ alkyl group e.g. a methyl group; $R_2$ represents a hydrogen atom or a $C_{1-3}$ alkyl group, e.g. a methyl, ethyl or isopropyl group, a $C_{3-4}$ alkenyl group e.g. a propenyl group or an ar($C_{1-2}$)alkyl group e.g. a benzyl group; $R_3$ represents a hydrogen atom; and $R_4$ and $R_5$, which may be the same or different, each represents a hydrogen atom or a $C_{1-3}$ alkyl group e.g. a methyl group; and physiologically acceptable salts and solvates (e.g. hydrates) thereof.

A particularly preferred class of compounds according to the invention is that wherein $R_1$ represents a hydrogen atom or a $C_{1-3}$ alkyl group e.g. a methyl group; $R_2$ represents a $C_{1-3}$ alkyl group e.g. a methyl group, or a $C_{3-4}$ alkenyl group e.g. a propenyl group; $R_3$ and $R_4$ each represents a hydrogen atom; and $R_5$ represents a hydrogen atom or a $C_{1-3}$ alkyl group e.g. a methyl group; and physiologically acceptable salts and solvates (e.g. hydrates) thereof.

Preferred compounds according to the invention include:

3-(2-(methylamino)ethyl)-N-methyl-1H-indole-5-methanesulphonamide;

3-(2-aminoethyl)-N,N-dimethyl-1H-indole-5-methanesulphonamide;

3-(2-aminoethyl)-N-(2-propenyl)-1H-indole-5-methanesulphonamide;

and physiologically acceptable salts and solvates (e.g. hydrates) of these compounds.

A particularly preferred compound according to the invention is:

3-(2-aminoethyl)-N-methyl-1H-indole-5-methanesulphonamide and the physiologically acceptable salts (e.g. the hydrochloride and succinate salts) and solvates (e.g. hydrates) thereof.

According to another aspect of the invention, compounds of general formula (I) and their physiologically acceptable salts and solvates (e.g. hydrates) may be prepared by the general methods outlined hereinafter. In the following processes, $R_1$, $R_2$, $R_3$, $R_4$, $R_5$, and Alk are as defined for the general formula (I) unless otherwise specified.

According to a general process (A), compounds of general formula (I) may be prepared by cyclisation of compounds of general formula (II):

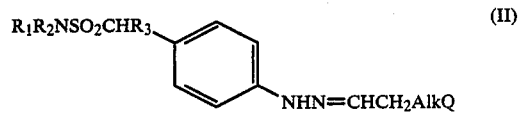

(II)

(wherein Q is the group $NR_4R_5$ or a protected derivative thereof or a leaving group such as a halogen atom (e.g. chlorine or bromine), or an acyloxy group such as acetoxy, chloroacetoxy, dichloroacetoxy, trifluoroacetoxy or p-nitrobenzoyloxy or a sulphonate group such as p-toluene sulphonate or methyl sulphonate).

Particularly convenient embodiments of the process are described below.

When Q is the group $NR_4R_5$ (or a protected derivative thereof), the process is desirably carried out in a suitable reaction medium, such as an aqueous organic solvent, for example, an aqueous alcohol (e.g. methanol, ethanol and isopropanol) or aqueous ether (e.g. dioxan) in the presence of an acid catalyst. (In some cases the acid catalyst may also act as the reaction solvent). Suitable acid catalysts include inorganic acids such as sulphuric or hydrochloric acid or organic carboxylic acids such as acetic acid. Alternatively the cyclisation may be carried out using polyphosphate ester in a chlorinated solvent (e.g. chloroform) or using a Lewis acid such as zinc chloride in ethanol or boron trifluoride in acetic acid. The reaction may conveniently be carried out at temperatures of from 20° to 200° C., preferably 50° to 125° C.

When Q is a leaving group, such as a chlorine or bromine atom, the reaction may be effected in an aqueous organic solvent, such as an aqueous alcohol (e.g. methanol, ethanol or isopropanol) or an aqueous ether (e.g. dioxan), in the absence of an inorganic acid, conveniently at a temperature of from 20° to 200° C., preferably 50° to 125° C. This process results in the formation of a compound of formula (I) wherein $R_4$ and $R_5$ are both hydrogen atoms.

According to a particular embodiment of this process, compounds of general formula (I) may be prepared directly by the reaction of a compound of general formula (III):

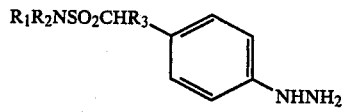  (III)

or a salt (e.g. the hydrochloride salt) thereof, with a compound of formula (IV):

HCOCH₂AlkQ     (IV)

(wherein Q is as defined above) or a salt or protected derivative thereof (such as an acetal, for example, a dialkyl or cyclic acetal e.g. formed with an appropriate alkyl orthoformate or diol or protected as a bisulphite addition complex), using the appropriate conditions as described above for the cyclisation of a compound of general formula (II) (The Fischer-Indole Synthesis, B. Robinson p 488—Wiley 1982).

Compounds of general formula (II) may, if desired, be isolated as intermediate by reacting a compound of formula (III), or a salt or protected derivative thereof with a compound of formula (IV) or a salt or protected derivative thereof, in a suitable solvent, such as an aqueous alcohol (e.g. methanol) or an aqueous ether (e.g. dioxan) and at a temperature of, for example, from 20° to 30° C. If an acetal of a compound of formula (IV) is used it may be necessary to carry out the reaction in the presence of an acid (for example, acetic or hydrochloric acid).

As illustrated in the following general processes (B) and (C), the aminoalkyl substituent—AlkNR₄R₅ may be introduced at the 3-position by a variety of conventional techniques which may, for example, involve modification of a substituent at the 3-position or direct introduction of the aminoalkyl substituent into the 3-position.

Thus a further general process (B) for preparing compounds of general formula (I) involves reacting a compound of general formula (V):

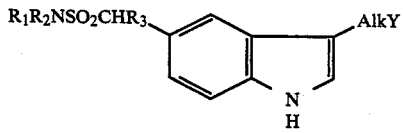  (V)

(wherein Y is a readily displaceable group) or a protected derivative thereof, with a compound of formula R₄R₅NH.

This displacement reaction may conveniently be carried out on those compounds of formula (V) wherein the substituent group Y is a halogen atom (e.g. chlorine, bromine or iodine) or a group OR where OR is, for example, an acyloxy group, such as acetoxy, chloroacetoxy, dichloroacetoxy, trifluoroacetoxy or p-nitrobenzoyloxy or a sulphonate group (e.g. p-toluene sulphonate or methyl sulphonate).

The above reaction is conveniently effected in an inert organic solvent (optionally in the presence of water), examples of which include alcohols, e.g. ethanol; ethers, e.g. tetrahydrofuran; esters e.g ethyl acetate; amides e.g. N,N-dimethylformamide; and ketones e.g. acetone. The process may be carried out at a temperature of, for example, −10° to +150° C., preferably 20° to 50° C.

The compounds of formula (V) wherein Y is a halogen atom may be prepared by reacting a hydrazine of formula (III) with an aldehyde (or a protected derivative thereof) of formula (IV) in which Q is a halogen atom, in an aqueous alcohol (e.g. methanol) or an aqueous ether (e.g. dioxan) containing an acid (e.g. acetic or hydrochloric acid) or by reacting a compound of general formula (V) wherein Y is a hydroxy group with the appropriate phosphorus trihalide. The intermediate alcohol, wherein Y is a hydroxy group, may also be used to prepare compounds of formula (V), wherein Y is a group OR, by acylation or sulphonylation with the appropriate activated species (e.g. an anhydride or sulphonyl chloride) using conventional techniques.

Compounds of general formula (I) may also be prepared by another general process (C) involving reduction of a compound of general formula (VI):

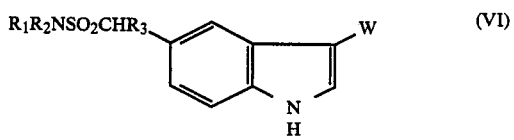  (VI)

(wherein W is a group capable of being reduced to give the required AlkNR₄R₅ group or a protected derivative thereof) or a salt or protected derivative thereof.

The required Alk and NR₄R₅ groups may be formed by reduction steps which take place separately or together in any appropriate manner.

Examples of groups represented by the substituent group W include the following:

TNO₂ (where T is Alk or an alkenyl group corresponding to the group (Alk); AlkN₃; AlkNR₄COR₅′; —COCONR₄R₅; (CHR₆)ₓCHR₇CN; CHR₇COZ; (CHR₆)ₓCR₇=NOH; CH(OH)CHR₇NR₄R₅; COCHR₇Z (where R₆ and R₇ which may be the same or different, each represents a hydrogen atom or a C₁₋₃ alkyl group, Z is an azido group N₃ or the group NR₄R₅ or a protected derivative thereof, x is zero or 1 and R₅′ is part of the group R₅ or the group OR_c where R_c is an alkyl or an aralkyl group).

Groups which may be reduced to the group Alk include corresponding unsaturated groups and corresponding groups containing one or more hydroxyl groups or carbonyl functions.

Groups which may be reduced to the group NR₄R₅ wherein R₄ and R₅ are both hydrogen include nitro, azido, hydroxyimino and nitrile groups. Reduction of a nitrile group yields the group CH₂NH₂ and thus provides a methylene group of the group Alk.

The required NR₄R₅ group wherein R₄ and/or R₅ are other than hydrogen may be prepared by reduction of a nitrile (CHR₆)ₓCHR₇CN or an aldehyde (CHR₆)ₓCHR₇CHO (where R₆, R₇ x are as previously defined) in the presence of an amine, R₄R₅NH.

A particularly suitable method for preparing a compound of formula (I) wherein R₄ and/or R₅ is other than hydrogen, is reductive alkylation of the corresponding compound wherein R₄ and/or R₅ represents hydrogen, with an appropriate aldehyde or a ketone (e.g. acetaldehyde or benzaldehyde or acetone) in the presence of a suitable reducing agent. In some instances (e.g. for the introduction of the group R₅ where R₅ is ethyl) the aldehyde (e.g. acetaldehyde) may be condensed with the primary amine and the intermediate thus formed may subsequently be reduced using a suitable reducing agent.

A compound of general formula (I) where $R_5$ is a hydrogen atom, may also be prepared by reduction of a corresponding compound of general formula (I) wherein $R_5$ is a benzyl group, for example with hydrogen in the presence of a catalyst e.g. 10% palladium on carbon.

The required $NR_4R_5$ group wherein $R_4$ and/or $R_5$ are other than hydrogen may also be prepared by reduction of a corresponding amide, for example, $AlkNR_4COR_5'$ (where $R_5'$ is as previously defined).

It will be appreciated that the choice of reducing agent and reaction conditions will be dependent on the nature of the group W.

Suitable reducing agents which may be used in the above process for the reduction of compounds of formula (VI) wherein W represents, for example, the groups $TNO_2$, $AlkN_3$, $(CHR_6)_xCHR_8CN$, $(CHR_6)_xCR_7=NOH$, $CH(OH)CHR_7NR_4R_5$ (where T, $R_5'$, $R_6$ and $R_7$ and x are as previously defined) include hydrogen in the presence of a metal catalyst, for example Raney Nickel or a noble metal catalyst such as platinum, platinum oxide, palladium or rhodium, which may be supported, for example, on charcoal, kieselguhr or alumina. In the case of Raney Nickel hydrazine may also be used as the source of hydrogen. This process may conveniently be carried out in a solvent such as an alcohol e.g. ethanol, an ether, e.g. dioxan or tetrahydrofuran, an amide, e.g. dimethylformamide or an ester e.g. ethyl acetate, and at a temperature of from $-10°$ to $+50°$ C., preferably $-5°$ to $+30°$ C.

The reduction process may also be effected on compounds of formula (VI) wherein W represents, for example, the groups $TNO_2$, $AlkN_3$, $CH(OH)CHR_7NR_4R_5$ or $COCHR_7Z$ (where T, $R_7$ and Z are as previously defined), using an alkali metal or alkaline earth metal borohydride or cyanoborohydride e.g. sodium or calcium borohydride or cyanoborohydride which process may conveniently be carried out in an alcohol such as propanol or ethanol and at a temperature of from $10°$ to $100°$ C., preferably $50°$ to $100°$ C. In some instances the reduction using a borohydride may be carried out in the presence of cobaltous chloride.

Reduction of compounds of formula (VI) wherein W represents, for example, the groups $TNO_2$, $AlkN_3$, $AlkNR_4COR_5'$, $CHR_7COZ$, $(CHR_6)_xCR_7=NOH$, $CH(OH)CHR_7NR_4R_5$, $-COCONR_4R_5$ and $COCHR_7Z$ (wherein T, $R_5'$, $R_6$, $R_7$, Z and x are as previously defined) may also be carried out using a metal hydride such as lithium aluminium hydride. This process may be carried out in a solvent, for example, an ether such as tetrahydrofuran, and conveniently at a temperature of from $-10°$ to $+100°$ C., preferably $50°$ to $100°$ C.

A particular embodiment of this process includes the reduction of a compound of formula (VI) wherein W is the group $CHR_7CN$, for example, by catalytic reduction with hydrogen in the presence of a catalyst such as palladium or rhodium on alumina, optionally in the presence of an amine $HNR_4R_5$, or using lithium aluminium hydride.

The starting materials or intermediate compounds of general formula (VI) may be prepared by analogous methods to those described in U.K. Published Patent Application No. 2035310 and "A Chemistry of Heterocyclic Compound—Indoles Part II" Chapter VI edited by W. J. Houlihan (1972) Wiley Interscience, New York.

A compound of formula (VI) wherein W is the group $AlkNHCOR_5'$ may be prepared by acylation of the corresponding unsubstituted amine using conventional techniques.

The Fischer-indole cyclisation process may be employed to prepare a compound of formula (VI) wherein W is the group $(CHR_6)_xCHR_7CN$ or $CHR_6CHR_7NO_2$ in conventional manner.

The following reactions (D), in any appropriate sequence, may if necessary and/or desired be carried out subsequent to any of the above described processes:
 (i) conversion of one compound of general formula (I) or a salt or protected derivative thereof into another compound of general formula (I);
 (ii) removal of any protecting groups; and
 (iii) conversion of a compound of general formula (I) or a salt thereof into a physiologically acceptable salt or solvate (e.g. hydrate) thereof.

Thus, a compound of formula (I) according to the invention may be converted into another compound of the invention using conventional procedures.

For example, a compound of general formula (I) wherein one or more of $R_1$, $R_2$, $R_4$ and $R_5$ are alkyl groups may be prepared from the corresponding compounds of formula (I) wherein one or more of $R_1$, $R_2$, $R_4$ and $R_5$ represent hydrogen atoms, by reaction with a suitable alkylating agent such as an alkyl halide (e.g. methyl or ethyl iodide), alkyl tosylate (e.g. methyl tosylate) or dialkylsulphate (e.g. dimethylsulphate). The alkylation reaction is conveniently carried out in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides, such as sodium hydride, alkali metal amides, such as sodium amide, alkali metal carbonates, such as sodium carbonate or alkali metal alkoxides such as sodium or potassium methoxide, ethoxide or t-butoxide.

It should be appreciated that in some of the above transformations it may be necessary or desirable to protect any sensitive groups in the molecule of the compound in question to avoid undesirable side reactions. For example, during any of the reaction sequences described above, it may be necessary to protect the group $NR_4R_5$, wherein $R_4$ and/or $R_5$ represents hydrogen, with a group easily removable at the end of the reaction sequence. Such groups may include, for example, aralkyl groups, such as benzyl, diphenylmethyl or triphenylmethyl; or acyl groups such as N-benzyloxycarbonyl or t-butoxycarbonyl or phthaloyl.

In some cases, it may also be desirable to protect the indole nitrogen with, for example, an aralkyl group such as benzyl.

Subsequent cleavage of the protecting group may be achieved by conventional procedures. Thus an aralkyl group such as benzyl, may be cleaved by hydrogenolysis in the presence of a catalyst (e.g. palladium on charcoal) or sodium and liquid ammonia; an acyl group such as N-benzyloxycarbonyl may be removed by hydrolysis with, for example, hydrogen bromide in acetic acid or by reduction, for example by catalytic hydrogenation. The phthaloyl group may be removed by hydrazinolysis (e.g. by treatment with hydrazine hydrate) or by treatment with a primary amine (e.g. methylamine).

Where it is desired to isolate a compound of the invention as a physiologically acceptable salt, for example as an acid addition salt, this may be achieved by treating the free base of general formula (I), with an appropriate acid (e.g. succinic or hydrochloric acid) preferably with an equivalent amount in a suitable solvent (e.g. aqueous ethanol).

The starting materials or intermediate compounds for the preparation of the compounds according to this invention may be prepared by conventional methods analogous to those described in U.K. Published patent application No. 2035310.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced either before or after cyclisation to form the indole nucleus. It should therefore be appreciated that in such multi-stage processes, the sequence of reactions should be chosen in order that the reaction conditions do not affect groups present in the molecule which are desired in the final product.

The invention is further illustrated by the following Examples. All temperatures are in °C. 'Hyflo' is a filtration aid. Chromatography was carried out using silica gel (Merck, Kieselgel 60, Art. 7734) and t.l.c.-thin layer chromatography, on silica (Macherly-Nagel, Polygram) except where otherwise stated. The following abbreviations define the eluent used for chromatography and t.l.c.

(A) Methylene chloride-ethanol-0.88 ammonia 100:8:1
(B) Methylene chloride-ethanol-0.88 ammonia 40:8:1
(C) Cyclohexane-ethyl acetate 1:4
(D) Ethyl acetate-toluene 1:1
(E) Ethyl acetate-toluene 3:7
(F) Methylene chloride-ethanol-0.88 ammonia 30:8:1
(G) Methylene chloride-ethanol-0.88 ammonia 150:8:1
(H) Methylene chloride-ethanol-0.88 ammonia 25:8:1
(I) Chloroform-methanol 97:3
(J) Methylene chloride-ethanol-0.88 ammonia 20:8:1
(K) Ether-isopropanol-water-0.88 ammonia 20:20:8:1
(L) Ethyl acetate-isopropanol-water-0.88 ammonia 25:15:8:2
(M) Methylene chloride-methanol 95:5
(N) Methylene chloride-ethanol-0.88 ammonia 50:8:1
(O) Methylene chloride-ethanol-0.88 ammonia 10:8:1
(P) Chloroform-methanol 95:5
(Q) Methylene chloride-ethanol-0.88 ammonia 200:8:1

Intermediates were routinely checked for purity by t.l.c. employing u.v. light for detection and spray reagents such as DNP and potassium permanganate. In addition indolic intermediates were detected by spraying with aqueous ceric sulphate and tryptamines by spraying with a solution of iodoplatinic acid or ceric sulphate.

Example 1

3-(2-Aminoethyl)-N-methyl-1H-indole-5-methanesulphonamide, maleate (a) 4-Amino-N-methylbenzenemethanesulphonamide, hydrochloride A suspension of N-methyl-4-nitrobenzenemethanesulphonamide (30 g) in ethanol (150 ml), water (300 ml) and hydrochloric acid (2N, 65 ml) was hydrogenated over 10% palladium oxide on charcoal (7.5 g, 50% paste with water) until hydrogen uptake ceased (9.75 l). The catalyst was removed by filtration through "hyflo" and the filter pad was washed with water (30 ml). The filtrate was evaporated under reduced pressure to give the title compound as a pale yellow powder (28.2 g) m.p. 143°-144° C.

(b) 4-Hydrazino-N-methylbenzenemethanesulphonamide, hydrochloride

A solution of sodium nitrite (13.72 g) in water (160 ml) was added slowly to a cooled stirred mixture of 4-Amino-N-methylbenzene methanesulphonamide (39.3 g), water (240 ml) and conc. hydrochloric acid (400 ml) such that the temperature did not exceed 0°. After stirring for 15 min this mixture was added slowly to a cold solution of stannous chloride dihydrate (221.1 g) in conc. hydrochloric acid (400 ml) again keeping the temperature below 0°. Once the addition was complete the mixture was allowed to warm to room temperature (1 h). The solid was collected by filtration, washed well with diethyl ether (4×250 ml) and dried at 45° to give the title compound as a white powder (31.6 g). An assay by periodate titration showed this to be 91.3% pure.

T.l.c. (A) Rf 0.4.

(c) 3-(2-Aminoethyl)-N-methyl-1H-indole-5-methanesulphonamide, maleate

A solution of 4-Hydrazino-N-methylbenzenemethanesulphonamide hydrochloride (10 g) and 4-chlorobutanal dimethyl acetal (6.5 g) in ethanol/water (5:1, 500 ml) was heated at reflux for 2 h. The solution was then cooled and evaporated to dryness under reduced pressure. The orange-brown residue was purified by column chromatography (B) to give the tryptamine as an oil (3.9 g). A solution of this material (3.9 g) in ethanol (50 ml) and methanol (10 ml) was treated with a solution of maleic acid (1.7 g) in ethanol (10 ml) and the resulting solution was concentrated to a thick oil which solidified on cooling to give the title compound, m.p. 140°-1°.

Analysis Found: C, 50.1; H, 5.3; N, 10.6. $C_{12}H_{17}N_3O_2S \cdot C_4H_4O_4$ requires C, 50.1; H, 5.5; N, 11.0%.

T.l.c. (F) Rf 0.26.

Example 2

3-(2-Aminoethyl)-N-methyl-1H-indole-5-methanesulphonamide, maleate (a) 3-[2-(1,3-Dihydro-1,3-dioxo-2H-isoindol-2-yl)ethyl]-N-methyl-1H-indole-5-methanesulphonamide A suspension of the product of example 1(b) (7 g) and 2-(4,4-diethoxybutyl)-1H-isoindole-1,3(2H)-dione (8.15 g) in dilute acetic acid (25%, 450 ml) was stirred at room temperature for 0.5 h and then heated at reflux for 1 h. The resulting suspension was partitioned between water (1 l) and ethyl acetate (200 ml). The aqueous layer was extracted with more ethyl acetate (3×250 ml). The organic extracts were combined, washed with saturated sodium bicarbonate (to pH 7) and dried (MgSO₄). Evaporation of the solvent gave the title compound as a yellow-orange foam (4.5 g) which was used in the next stage without further purification.

T.l.c. (C) Rf 0.63 impurities at Rf 0.45 and 0.07.

(b) Phenylmethyl[2-[5-[[(methylamino)sulphonyl]methyl]-1H-indol-3-yl]ethyl]carbamate A hot solution of the product of stage (a) (4.5 g) in ethanol (70 ml) was treated with hydrazine hydrate (2.8 ml) and heated at reflux for 2 h. Solvent was evaporated, the residual solid suspended in sodium carbonate (2N; 50 ml) and tetrahydrofuran (20 ml) and treated with benzyl chloroformate (3.15 ml). After 2 h the aqueous layer was extracted with ethyl acetate (4×50 ml), the extract dried (MgSO$_4$) and solvent evaporated. Chromatography (D) gave the title compound as a yellow foam (2.5 g) which was used in the next stage without further purification.

T.l.c. (E) Rf 0.35

(c) 3-(2-Aminoethyl)-N-methyl-1H-indole-5-methanesulphonamide, maleate

A solution of the product of stage (b) (0.85 g) in methanol (10 ml) was hydrogenated over pre-reduced palladium oxide on carbon (10%, 300 mg) at room temperature and atmospheric pressure for 6 h (uptake of hydrogen 30 ml). The catalyst was filtered off (hyflo) and washed with methanol (100 ml). The filtrate was concentrated and the residual white solid (0.56 g) purified by column chromatography (F) to give the tryptamine as a white foam (0.26 g). Part of this (0.13 g) in absolute ethanol (5 ml) was treated with maleic acid (0.052 g) and the solvent was evaporated. The residual oil crystallised from tetrahydrofuran (5 ml) with a few drops of ethanol to give the title compound as an off-white solid, m.p. 150°–4° (0.11 g).

Analysis Found: C, 50.2; H, 5.6; N, 10.7. $C_{12}H_{17}N_3O_2S.C_4H_4O_4$ requires: C, 50.1; H, 5.5; N, 10.9%

T.l.c. (F) Rf 0.26.

Example 3

3-(2-Aminoethyl-N-methyl-1H-indole-5-methanesulphonamide (a) 4-[2-(3-Cyanopropylidene)hydrazino]-N-methyl-benzenemethanesulphonamide A solution of the product of example 1(b) (2 g) and 3-cyanopropanal dimethylacetal (1.4 g) in water (25 ml) was treated with dilute hydrochloric acid (2N; 5 drops) and stirred for 24 h at room temperature. The resulting white solid was filtered off, washed with water (20 ml), ether (100 ml) and dried in vacuo at 40° to give the title compound (2.1 g) m.p. 124°–125°.

(b) 3-(Cyanomethyl)-N-methyl-1H-indole-5-methanesulphonamide

A suspension of the product from stage (a) (0.7 g) in polyphosphate ester (7 g) and chlorform (14 ml) was heated at reflux for 5 min. and then poured onto ice. The resulting suspension was stirred with ice for 20 min., then extracted with chloroform (4×20 ml) and the extract dried. Solvent was then removed and the residue purified by column chromatography (G). The title compound was obtained as a reddish semi-solid (0.38 g) which was impure and was employed directly in the next stage.

T.l.c. (G) Rf 0.4 with impurities at Rf 0.44 and 0.46.

(c) 3-(2-Aminoethyl)-N-Methyl-1H-indole-5-methanesulphonamide

A solution of the product of stage (b) (0.15 g) in methanolic ammonia was hydrogenated over pre-reduced rhodium on alumina (5%, 0.15 g) for 18 h at room temperature and atmospheric pressure. T.l.c. (F) showed the solution contained a major component Rf 0.26 identical with tht of 3-(2-aminoethyl)-N-methyl-1H-indole-5-methanesulphonamide prepared by the method of example 1.

Example 4

3-(2-Aminoethyl)-N-methyl-1H-indole-5-methanesulphonamide

To a solution of the product of example 3(b) (0.15 g) in dry tetrahydrofuran (20 ml) was added lithium aluminium hydride (0.15 g) and the resulting suspension was heated at reflux (under a nitrogen atmosphere) for 1 h. Excess lithium aluminium hydride was destroyed by addition of ethyl acetate (5 ml), followed by addition of aqueous potassium carbonate (10 ml; saturated). The aqueous layer was extracted with ethanol (10 ml). Solvent was evaporated under reduced pressure, and the residual oil purified by column chromatography (H) to give the title compound slightly impure as an oil (21 mg) which was shown by n.m.r. and t.l.c. (F) Rf 0.26 to be identical with a sample prepared by the method of example 1.

Example 5

3-(2-Aminoethyl)-N-methyl-1H-indole-5-methanesulphonamide (a) N-Methyl-4-[2-(4-Nitrobutylidene)hydrazino]-benzenemethanesulphonamide To a solution of the product of example 1(b) (1 g) in water (20 ml) was added 4-nitrobutanal (0.5 g) and an oil separated within a few minutes. The resulting suspension was extracted with dichloromethane (4×20 ml), the extracts dried (MgSO$_4$) and the solvent evaporated in vacuo to give the title compound as a thick oil (1.08 g)

Analysis Found: C, 45.3; H, 5.6; N, 17.3. $C_{12}H_{18}N_4O_4S.0.2H_2O$ requires C, 45.6; H, 5.2; N, 17.7%.

T.l.c. isopropyl acetate/cyclohexane (3:1) Rf 0.26.

(b) N-Methyl-3-(2-nitroethyl)-1H-indole-5-methanesulphonamide

A solution of the product of stage (a) (2 g) in chloroform (40 ml) and polyphosphate ester (20 g) was heated under reflux for 3 min. and then poured onto ice (50 g) and sodium bicarbonate (8%, 20 ml). The mixture was stirred at room temperature for 30 minutes and extracted with chloroform (4×50 ml). The organic extracts were dried (MgSO$_4$) and concentrated. The residue was purified by flash chromatography (Merck 9385) (I) to give the title compound as an oil (0.72 g) which was used in the next stage without further purification.

T.l.c. (Q) Rf 0.26. N.m.r. 5.2$\tau$ (triplet CH$_2$NO$_2$).

(c) 3-(2-Aminoethyl)-N-methyl-1H-indole-5-methanesulphonamide

A solution of the product of stage (b) (0.13 g) in ethyl acetate (5 ml) was hydrogenated over pre-reduced 10% palladium oxide on charcoal (0.2 g, 50% paste with water) for 2 h, whereupon hydrogen uptake (20 ml) ceased. The catalyst was removed by filtration (hyflo) and the filtrate concentrated. The residue was purified by flash chromatography (Kiselgel 9385) to give the title compound (8 mg) as an oil which was shown by t.l.c. (F) Rf 0.26 to be identical with the product of example 1.

Example 6

3-(2-Aminoethyl)-N-methyl-1H-indole-5-methanesulphonamide (a) 4-[2-(4-Chlorobutylidene)hydrazino]-N-methylbenzenemethanesulphonamide A mixture of the product of example 1(b) (0.54 g), 4-chlorobutanal dimethyl acetal (0.30 g), water (4 ml) and hydrochloric acid (2N; 2 drops) was stirred at room temperature for 1.5 h. The mixture was filtered, and the solid was washed with water (20 ml), air-dried (1 h), and dried overnight in vacuo over phosphorus pentoxide to give the title compound as a cream solid (0.44 g), m.p. 77°–79° (dec.).

(b) 3-(2-Chloroethyl)-N-methyl-1H-indole-5-methanesulphonamide

A solution of the product from stage (a) (0.29 g) in chloroform (3 ml) was added to a solution of polyphosphate ester (2.92 g) in chloroform (2 ml), and the yellow solution was heated at reflux for 5 min. The resulting brown solution was then immediately poured onto ice (ca 20 g), carefully diluted with sodium bicarbonate solution (8%; ca 50 ml) until basic, and stirred at room temperature for 15 min. The mixture was then extracted with chloroform (3×20 ml), and the combined organic extract was washed with brine (20 ml), dried ($MgSO_4$) and evaporated in vacuo to give the title compound crude as a yellow-brown oil (0.60 g) which was used in the next step without further purification.

T.l.c. (I) major components Rf 0.25, 0.32, minor products Rf 0.0, 0.05, 0.43 and 0.57.

(c) 3-(2-Aminoethyl)-N-methyl-1H-indole-5-methanesulphonamide

A solution of the product of stage (b) (0.60 g) in methanol (4 ml) was diluted with ammonium hydroxide (30 ml), and the suspension was stirred in an autoclave at 90° for 110 min. The mixture was filtered, and the filtrate was evaporated in vacuo to give a yellow gum, which was azeotroped with absolute ethanol (2×30 ml) to give a sticky solid (0.46 g). This material was purified by chromatography (J) to give the title compound as a pale yellow oil (0.036 g) shown by t.l.c. (J) Rf 0.23 and n.m.r. to be identical with that of the product of example 1.

Example 7

3-(2-Aminoethyl)-N-methyl-1H-indole-5-methanesulphonamide, hydrochloride

To a solution of the tryptamine free base (0.267 g) prepared by the method of example 1 in ethanol (3 ml) was added 3.1N ethanolic hydrogen chloride until the solution was just acidic. The yellow solution was heated to boiling and on cooling the title compound separated as pale cream micro needles (0.26 g), m.p. 229°–231° C.

Analysis Found: C, 47.7; H, 6.1; N, 13.4. $C_{12}H_{17}N_3O_2S.HCl$ requires C, 47.4; H, 6.0; N, 13.8%.

T.l.c. (J) Rf 0.3.

Example 8

3-(2-Aminoethyl)-N-methyl-1H-indole-5-methanesulphonamide, hemisuccinate

To a hot solution of the tryptamine free base (0.267 g) prepared by the method of example 1 in ethanol (3 ml) was added a hot solution of succinic acid (0.059 g) in ethanol (3 ml). On cooling the title compound separated as an off-white powder (0.29 g), m.p. 179°–181° C.

Analysis Found: C, 51.5; H, 6.2; N, 12.6. $C_{12}H_{17}N_3O_2S.0.5C_4H_6O_4$ requires C, 51.5; H, 6.2; N, 12.9%.

T.l.c. (J) Rf 0.30.

Example 9

3-(2-Aminoethyl)-N-(phenylmethyl)-1H-indole-5-methanesulphonamide, compound with creatinine, sulphuric acid and water (1:1:1:1.2)

(a) 4-Nitro-N-(phenylmethyl)benzenemethanesulphonamide

Benzylamine (0.8 ml) was added in one portion to a solution of 4-nitrobenzenemethanesulphonyl chloride (0.6 g) in dichloromethane (50 ml) stirred at ambient temperature. A white solid precipitated at once. Stirring was continued for 1 h, solvent was evaporated and the residual solid washed with water (100 ml), ether (200 ml) and dried. The title compound was obtained as a white solid (0.64 g) m.p. 180°–1°. A sample (0.2 g) was recrystallised from hot ethanol (5 ml) to give analytically pure material as an off-white solid (0.15 g), m.p. 182°–3°.

(b) 4-Amino-N-(phenylmethyl)benzenemethanesulphonamide

A suspension of the product of stage (a) (5 g) in methanol (150 ml) was hydrogenated over pre-reduced 10% palladium oxide on charcoal (1 g) at room temperature and pressure. Hydrogen uptake was complete in 20 min. after 1.1 l had been absorbed. Catalyst was filtered off (hyflo), washed with more methanol (500 ml) and the solvent evaporated. The product was obtained as an off-white solid (3.75 g), m.p. 116°–7°. A small sample (0.15 g) was crystallised from hot methanol (3 ml) and few drops of ether to give the title compound (0.1 g) m.p. 117°–118°.

(c) 4-Hydrazino-N-(phenylmethyl)benzenemethanesulphonamide, hydrochloride

A thick suspension of the product of stage (b) (3.68 g) in conc. hydrochloric acid (50 ml) was stirred at −5° whilst a solution of sodium nitrite (0.9 g) in water (10 ml) was added dropwise so that temperature did not exceed 0°. Stirring was continued for 30 min. The resulting suspension was filtered to remove starting material and the filtrate added in a few portions to a solution of stannous chloride dihydrate (13.5 g) in hydrochloric acid (15 ml) at −20° and warmed to ambient temperature. The solid that separated was filtered off and recrystallised from hot methanol (100 ml) to give the title compound as white plates (0.39 g) m.p. 192°–193°. The mother liquors afforded a second crop (0.52 g).

(d) 3-(2-Aminoethyl)-N-(phenylmethyl)-1H-indole-5-methanesulphonamide, compound with creatinine, sulphuric acid and water (1:1:1:1.2)

A solution of the product of stage (c) (0.47 g) and 4-chlorobutanal dimethylacetal (0.24 g) in ethanol (50 ml) and water (10 ml) was heated at reflux for 4 h. Solvent was evaporated and the residual oil purified by column chromatography (F) which afforded the tryptamine slightly impure as an oil (0.34 g). A second chromatography (K) gave pure free base as an oil (0.1 g) which was taken up in hot ethanol (8 ml) and water (1 ml) and treated with a solution of creatinine and sulphuric acid (1:1, 2N, 0.15 ml). The salt which crystallised on cooling was filtered off, dried in vacuo at 60° (16 h) and the title compound obtained as an off-white product (0.125 g), m.p. 230°–231°.

Analysis Found: C, 45.9; H, 5.7; N, 14.6. $C_{18}H_{21}N_3O_2S \cdot C_4H_7N_3O \cdot H_2SO_4 \cdot 1.2H_2O$ requires: C, 45.7; H, 5.3; N, 14.2%.

T.l.c. (K) Rf 0.41.

Example 10

3-(2-Aminoethyl)-N-phenyl-1H-indole-5-methanesulphonamide, compound with creatinine, sulphuric acid and water (1:1:1:1)

(a) 4-Amino-N-phenylbenzenemethanesulphonamide

A solution of 4-Nitro-N-phenylbenzenemethanesulphonamide (11.0 g), in ethyl acetate (400 ml) was hydrogenated at room temperature and pressure over pre-reduced 10% palladium oxide on charcoal (1.0 g, 50% paste with water) for 4 h until hydrogen uptake ceased (2.7 l). Methanol (400 ml) was added, the catalyst filtered off, and the filtrate evaporated in vacuo to give the title compound as a white solid (8.98 g), m.p. 180°–182°.

(b) 4-Hydrazino-N-phenylbenzenemethanesulphonamide, hydrochloride

By a procedure similar to that described in example 9(c), the product of stage (a) (7.4 g) was diazotised and then reduced with stannous chloride to give the title compound as a fawn solid (2.0 g), m.p. 168°–170° (from ethanol).

(c) 3-(2-Aminoethyl)-N-phenyl-1H-indole-5-methanesulphonamide, compound with creatinine, sulphuric acid and water (1:1:1:1)

By a procedure similar to that described in example 9(d), the product of stage (b) (0.5 g) was condensed with 4-chlorobutanal dimethyl acetal (0.25 g) to give the tryptamine as an oil. The oil was dissolved in a hot mixture of ethanol (40 ml) and water (5 ml) and an aqueous solution of creatinine and sulphuric acid (1:1, 2M; 0.9 ml) added. Filtration of the cooled mixture gave the title compound as a pale fawn solid (0.3 g), m.p. 198°–200°.

Analysis Found: C, 45.6; H, 5.4; N, 14.8. $C_{17}H_{19}N_3O_2S \cdot C_4H_7N_3O \cdot H_2SO_4 \cdot H_2O$ requires C, 45.2; H, 5.4; N, 15.0%.

T.l.c. (L) Rf 0.4.

Example 11

3-(2-Aminoethyl)-N-cyclohexyl-1H-indole-5-methanesulphonamide, compound with creatinine, sulphuric acid, and water (1:1:1:1)

(a) N-Cyclohexyl-4-nitrobenzenemethanesulphonamide

By a procedure similar to that described in example 9(a) 4-nitro-benzenemethanesulphonyl chloride (0.3 g) was treated with cyclohexylamine (0.36 ml) to give the title compound (0.25 g) m.p. 170°–171° (from ethanol).

(b) 4-Amino-N-cyclohexylbenzenemethanesulphonamide

By a procedure similar to that described in example 9(b) the product of stage (a) (6.4 g) was hydrogenated to give the title compound (5.0 g), m.p. 141°–143° (from isopropanol).

(c) N-Cyclohexyl-4-hydrazinobenzenemethanesulphonamide, hydrochloride

By a procedure similar to that described in example 9(c) the product of stage (b) (1.0 g) was diazotised and then reduced with stannous chloride to give the title compound as a white solid (0.25 g), m.p. 158°–160°, 90% pure.

T.l.c. (N) Rf 0.16.

(d) 3-(2-Aminomethyl)-N-cyclohexyl-1H-indole-5-methanesulphonamide, compound with creatinine, sulphuric acid, and water (1:1:1:1)

By a procedure similar to that described in example 9(d) the product of stage (c) (0.19 g) was condensed with 4-chlorobutanal dimethyl acetal (0.09 g) and flash chromatographed (Kieselgel 9385) (B) to give the tryptamine as a colourless glass (0.1 g) which was dissolved in a hot mixture of ethanol (9 ml) and water (1 ml) and treated with a solution of creatinine and sulphuric acid (2M, 1:1, 0.15 ml). On cooling and scratching the title compound was deposited as a pale cream-coloured crystalline solid (0.1 g), m.p. 218°–221° (dec) after drying in vacuo over $P_2O_5$ for 10 h at 60°.

Analysis Found: C, 44.7; H, 6.1; N, 14.7. $C_{17}H_{25}N_3O_2S \cdot C_4H_7N_3O \cdot H_2SO_4 \cdot H_2O$ requires C, 44.7; H, 6.4; N, 14.9%.

Example 12

3-(2-Aminoethyl)-N,N-dimethyl-1H-indole-5-methanesulphonamide, maleate.

(a) 4-Amino-N,N-dimethylbenzenemethanesulphonamide

A suspension of N,N-dimethyl-4-nitrobenzenemethanesulphonamide (4.2 g) in methanol (300 ml) was hydrogenated over pre-reduced 10% palladium oxide on charcoal (1 g) at atmospheric pressure and temperature. Hydrogen uptake was complete in 1 h. The catalyst was filtered off (Hyflo), washed with ethyl acetate (400 ml), the solvent evaporated and the title compound obtained as a cream solid (3.3 g), m.p. 151°–2°.

(b) 4-Hydrazino-N,N-dimethylbenzenemethanesulphonamide, hydrochloride

To a stirred suspension of the product of stage (a) (3.2 g) in conc. hydrochloric acid (35 ml) and water (17 ml) at −5° (ice-salt bath) was added a solution of sodium nitrite (1.1 g) in water (3 ml) at such a rate that the temperature did not exceed 0°. After stirring for 10 min, the yellow solution was added to a solution of stannous chloride dihydrate (17 g) in conc. hydrochloric acid (40 ml) at −10° at such a rate that the temperature did not exceed 0° C. Stirring was continued for 1 h at room temperature, the solid was collected by filtration, washed with ether (500 ml) and dried in vacuo at room temperature. The crude product (2.95 g) was crystallised from hot ethanol (40 ml) and methanol (20 ml) to give the title compound as a white solid (1.6 g), m.p. 155°–6°.

(c) 3-(2-Aminoethyl)-N,N-dimethyl-1H-indole-5-methanesulphonamide, maleate

A solution of the product of stage (b) (1 g) and 4-chlorobutanal, dimethyl acetal (0.7 g) in ethanol:water (5:1, 50 ml) was heated at reflux for 1 h 40 min. The cooled solution was evaporated to dryness under reduced pressure. The red-brown residue was purified by column chromatography (B) to give the tryptamine as an oil (0.13 g). A solution of this in ethanol (5 ml) was treated with maleic acid (0.054 g) and then concentrated to a foam which was triturated with ether and dried in vacuo at 80° to give the title compound as a hygroscopic solid (0.06 g).

Analysis Found: C, 51.6; H, 6.0; N, 10.1. $C_{13}H_{19}N_3O_2S \cdot C_4H_4O_4$ requires C, 51.4; H, 5.8; N, 10.6%.

T.l.c. (F) Rf 0.34.

In another experiment a hot solution of the tryptamine (0.07 g) in ethanol:water (8:1, 6 ml) was treated with a solution of creatinine and sulphuric acid (1:1, 0.125 ml, 2N) added in one portion and on cooling, the title compound crystallised as the creatinine sulphate adduct (85 mg), m.p. 197°–198°, dried at 60°.

Analysis Found: C, 40.3; H, 5.7; N, 16.1. $C_{13}H_{19}N_3O_2S \cdot C_4H_7N_3O \cdot H_2SO_4 \cdot H_2O$ Requires C, 40.0; H, 5.9; N, 16.5%.

Example 13

3-(2-Aminoethyl)-N-(2-phenylethyl)-1H-indole-5-methanesulphonamide, hydrochloride quarter hydrate (a) 4-Nitro-N-(2-phenylethyl)benzenemethanesulphonamide By a procedure similar to that described in example 9(a) 4-nitrobenzenemethanesulphonyl chloride (6.0 g) was condensed with 2-phenylethylamine (8 ml) to give the title compound as a light brown solid (7.5 g), m.p. 101°–103°.

(b) 4-Amino-N-(2-phenylethyl)benzenemethanesulphonamide

By a procedure similar to that described in example 9(b) the product of stage (a) (7.0 g) was hydrogenated in ethanol to give the title compound as a white solid (6.0 g), m.p. 123°–125° (from ethanol).

(c) 4-Hydrazino-N-(2-phenylethyl)benzenemethanesulphonamide, hydrochloride

By a procedure similar to that described in example 9(c) the product of stage (b) (4 g) was diazotised and reduced to give the title compound (3.0 g), m.p. 160°–163° (from ethanol).

(d) 3-(2-Aminoethyl)-N-(2-phenylethyl)-1H-indole-5-methanesulphonamide, hydrochoride, quarter hydrate By a procedure similar to that described in example 9(d) the product of stage (c) (2.0 g) was condensed with 4-chlorobutanal dimethyl acetal (1.0 g) and flash chromatographed (Kieselgel 9385) to give the tryptamine as a yellow oil. The oil was dissolved in methanol (10 ml) acidified with ethanolic hydrogen chloride (ca 2 ml) and diluted with ether (200 ml). The ether was decanted off the resulting gum, and replaced with more dry ether (200 ml). Scratching caused the gum to crystalline, and the resulting solid was filtered off, and dried in vacuo to give the title compound as a cream solid (0.65 g), m.p. 115°–119° C.

Analysis Found: C, 57.25; H, 6.2; N, 10.3. $C_{19}H_{23}N_3O_2S \cdot HCl \cdot 0.25H_2O$ requires C, 57.3; H, 6.2; N, 10.5%.

T.l.c. (J) Rf 0.4.

Example 14

3-(2-Aminoethyl)-N-(2-propenyl)-1H-indole-5-methanesulphonamide, hydrochloride (a) 4-Nitro-N-(2-propenyl)benzenemethanesulphonamide 4-Nitrophenylmethanesulphonyl chloride (5.0 g) was added dropwise in dry dichloromethane (50 ml) to a stirred solution of allylamine (3.3 ml) in dry dichloromethane (50 ml) at room temperature under nitrogen over 15 min. Stirring was continued for 45 min. The mixture was washed with water (3×50 ml), dried (MgSO$_4$) and the solvent evaporated to give a very pale yellow solid (5.22 g). A sample (0.26 g) was recrystallised from ethanol to give the title compound as very pale yellow needles (0.182 g), m.p. 118°–120.5°.

(b) 4-Amino-N-(2-propenyl)benzenemethanesulphonamide, hydrochloride

Sodium borohydride (0.37 g) in ethanol (120 ml) was added dropwise over 30 min to a stirred solution of the product of stage (a) (5.0 g) and stannous chloride dihydrate (22 g) in ethanol (400 ml) at 65° under nitrogen. After stirring at 65° for a further 30 min, the mixture was cooled in an ice bath, and iced water (400 ml) followed by 5N sodium hydroxide (40 ml, to pH 8) were added, giving a milky emulsion. The ethanol was evaporated at reduced pressure, more 5N sodium hydroxide (110 ml) was added, and the mixture was extracted with ethyl acetate (3×250 ml). The organic layers were washed with brine, dried (MgSO$_4$) and evaporated to give a yellow solid (4.96 g). A sample (0.3 g) was dissolved in ethanol (1.5 ml), and ethanolic hydrogen chloride (ca 3M, 0.6 ml) was added giving a pale yellow precipitate which was filtered off and dried in vacuo at 45°, to give the title compound as pale yellow crystals (0.239 g), m.p. 153.5°–155°.

(c) 4-Hydrazino-N-(2-propenyl)benzenemethanesulphonamide, hydrochloride

A solution of sodium nitrite (1.06 g) in water (2.5 ml) was added dropwise to a stirred suspension of the product from stage (b) (3.5 g) in 5N hydrochloric acid (28 ml) between −8° and −3° under nitrogen and stirring was continued at ca −3° for 80 min. The mixture was filtered, and the clear yellow filtrate was added dropwise from an ice-cooled, jacketed dropping funnel to a stirred solution of stannous chloride dihydrate (17.5 g) in concentrated hydrochloric acid (17.5 ml) between −2° and +1° over 35 min. After warming up to 10° over 15 min, the mixture was filtered, and the residue was washed with concentrated hydrochloric acid (4×30 ml) and dry ether (4×30 ml) and dried to give the title compound as a very pale yellow solid (2.44 g), m.p. 163°–166°, containing 5% inorganic material.

(d) 3-(2-Aminoethyl)-N-(2-propenyl)-1H-indole-5-methanesulphonamide, hydrochloride.

The product from stage (c) (1.5 g) was heated under reflux with 4-chlorobutanol dimethyl acetal (0.83 g) in 5:1 ethanol:water (75 ml) with stirring under nitrogen for 1.5 h. The mixture was poured into 8% aqueous sodium bicarbonate (25 ml), and the ethanol was evaporated off at room temperature (vacuum pump). The mixture was extracted with ethyl acetate (4×40 ml) and the organic layers were washed with brine, dried (MgSO$_4$) and evaporated to give a brown oil (1.62 g). Further extraction of the aqueous layers with butanone (3×40 ml), drying (MgSO$_4$) and evaporation gave a further quantity (0.3 g) of brown oil.

The combined crude products were purified by flash chromatography (Kieselgel 9385, H) to give a pale yellow foam (0.55 g). The foam was dissolved in absolute ethanol (2 ml), and ethanolic hydrogen chloride (ca 3M, 0.6 ml) was added giving a clear solution (pH 3). Addition of ethyl acetate (10 ml) followed by dry ether (60 ml) gave a white precipitate, which was triturated with dry ether (3×70 ml), filtered off and dried in vacuo at room temperature, to present the title compound as a powdery white solid (0.484 g), m.p. ca 90°–150° which was dried at 75°.

T.l.c. (L) Rf 0.45.

Analysis Found: C, 50.7; H, 5.9; N, 12.3. $C_{14}H_{19}N_3O_2S \cdot HCl$ requires C, 51.0; H, 6.1; N, 12.7%.

Example 15

3-(2-Aminoethyl)-N-(1-methylethyl)-1H-indole-5-methanesulphonamide compound with maleic acid (2:3)

(a) N-(1-Methylethyl)-4-nitrobenzenemethanesulphonamide

By a procedure similar to that described in example 9(a) 4-nitrobenzenemethanesulphonyl chloride (5 g) was reacted with isopropylamine (5.63 ml) to give the title compound (4.14 g) m.p. 146°–147° (from ethanol).

(b) 4-Amino-N-(1-methylethyl)benzenemethanesulphonamide

By a procedure similar to that described in example 9(b) the product of stage (a) was hydrogenated in ethanol to give the title compound (2.45 g) m.p. 105°–107° (from isopropanol)

(c) 4-Hydrazino-N-(1-methylethyl)benzenemethanesulphonamide, hydrochloride

By a procedure similar to that described in example 9(c) the product of stage (b) was diazotised and reduced to give the title compound as a white powder (1.5 g), 79% pure by periodate titration.

T.l.c. (A) Rf 0.36.

(d) 3-(2-Aminoethyl)-N-(1-methylethyl)-1H-indole-5-methanesulphonamide compound with maleic acid (2:3)

A mixture of the product of stage (c) (1.5 g) and 4-chlorobutanal dimethyl acetal (0.7 g) in a mixture of ethanol (35 ml) and water (5 ml) was heated at 50° for 30 min. Ammonium acetate (0.97 g) was added and the mixture heated at reflux for 4 h. The suspension was then diluted with water (200 ml) and the solid removed by filtration. The filtrate was washed with ethyl acetate (3×50 ml) and the washings discarded. The aqueous layer was basified by the addition of solid potassium carbonate (30 g) and the mixture extracted with ethyl acetate (4×50 ml), the extracts were dried ($Na_2SO_4$) and evaporated under reduced pressure. The residual oil was chromatographed (B) and the tryptamine (0.2 g) was dissolved in ethanol (5 ml), maleic acid (78.5 mg) in ethanol (5 ml) was added and the solution reduced to dryness to give a pale brown gum. Trituration with isopropanol (3×5 ml) gave the title compound as a pale brown powder (0.21 g) m.p. 150°–152°.

Analysis Found: C, 50.9; H, 5.9; N, 8.6. $C_{14}H_{21}N_3O_2S.1.5C_4H_4O_4$ requires C, 51.2; H, 5.8; N, 9.0%.

T.l.c. (H) Rf 0.30.

Example 16

3-(2-Aminoethyl)-N-ethyl-1H-indole-5-methanesulphonamide, maleate, hemihydrate compound with diethyl ether (10:10:5:1)

(a) 4-Amino-N-Ethylbenzenemethanesulphonamide

A solution of N-ethyl-4-nitrobenzenemethanesulphonamide (4.35 g) in warm ethanol (125 ml) was added to 10% palladium oxide on carbon (0.75 g, 50% aqueous paste) prereduced in ethanol (25 ml) and hydrogenated at atmospheric pressure. Hydrogen uptake (1400 ml) ceased after 20 minutes. The suspension was filtered and the catalyst was washed with methanol (100 ml) and ethanol (100 ml). Evaporation of the combined filtrate and washings produced a grey solid (2.0 g) which was crystallised from isoprpopanol (120 ml) to present the title compound as cream micro needles (1.48 g), m.p. 161°–164°.

(b) N-Ethyl-4-hydrazinobenzenemethanesulphonamide hydrochloride

Sodium nitrite (1.01) in water (12 ml) was slowly added to a stirred suspension at −5° of the finely ground product of stage (a) (3.14 g) in concentrated hydrochloric acid (30 ml) keeping the temperature below 0°. The resulting mixture was stirred at −5° for 15 min. the slowly added to a cold (−5°) stirred solution of stannous chloride (16.52 g) in concentrated hydrochloric acid (30 ml) keeping the solution below 0°.

After allowing the mixture to warm up to room temperature over a period of 1 h, the suspension was filtered and the solid washed with ether to give the title compound as a white solid (2.06 g), m.p. 169°–170°.

(c) 3-(2-Aminoethyl)-N-ethyl-1H-indole-5-methanesulphonamide maleate hemihydrate compound with diethylether (10:10:5:1)

A solution of the product of stage (b) (0.425 g) and 4-chlorobutanal dimethyl acetal (0.244 g) in ethanol-water (5:1) (20 ml) was stirred at 50° for 40 min. Ammonium acetate (0.7394 g) was added and then the pH of the solution adjusted to pH 4 by hydrochloric acid. The resultant solution was heated under reflux for 2 h.

The pale brown mixture was diluted water (200 ml) and washed with ethyl acetate (3×100 ml). The aqueous solution was basified with potassium carbonate (solid) and then extracted with ethyl acetate (4×100 ml). Subsequent evaporation of the dried ($MgSO_4$) organic extracts yielded a brown foam (0.38 g) which was purified by chromatography (N) to give the tryptamine as a pale brown gum (0.1435 g).

A solution of the base (0.1435 g, in methanol (2 ml) was treated with maleic acid (0.05916 g) in methanol (2 ml). Subsequent evaporation of the clear solution under reduced pressure gave a pale brown gum which was triturated with anhydrous diethyl ether to present the title compound as a cream powder (0.09 g), m.p. 139°–142°.

T.l.c. (H) Rf 0.4.

Analysis Found: C, 50.1; H, 5.8; N, 9.4. $C_{13}H_{19}N_3O_2S.C_4H_4O_4.0.5H_2O.0.1C_4H_{10}O$ C, 50.5; H, 6.1; N, 10.2%

Example 17

3-(2-Aminoethyl)-1H-indole-5-methanesulphonamide, hydrochloride (a) 4-Aminobenzenemethanesulphonamide A suspension of 4-nitrobenzenemethanesulphonamide (7.11 g) and 5% palladium oxide on charcoal (1.4 g) in ethanol (1.1 l) was hydrogenated at room temperature and pressure. The reaction was terminated after 2.5 l of hydrogen had been absorbed and the catalyst was removed by filtration. The filtrate was concentrated to give the title compoun as a solid (4.72 g). Recrystallisation of a sample from ethanol gave analytically pure material m.p. 166° (bubbles).

(b) 4-Hydrazinobenzenemethanesulphonamide hydrochloride

A solution of sodium nitrite (1.12 g) in water (10 ml) was added dropwise with stirring over a period of 10 min to a paste of the product of stage (a) (3.0 g) in conc. hydrochloric acid (4.8 ml) at 0° to −5°. The mixture was chilled to −5° and added in portions over 10 min to a vigorously stirred solution of sodium sulphite (5.02 g) and sodium acetate (5 g) in water (40 ml) at 0° to −5°. After 20 min the mixture was allowed to warm to room temperature over 1 h and was then heated at 75°–85° for 1 h. The solution was filtered and acidified with conc. hydrochloric acid (5.2 ml) and heated at 80°–85° and then more conc. hydrochloric acid (28 ml) was added. The solution was then chilled and the title compound separated as a cream solid (2.15 g), which was used in the next stage without further purification.

T.l.c. methanol-ethyl acetate, (1:4) Rf 0.6, 0.9 (minor).

(c) 3-[2-(1,3-Dihydro-1,3-dioxo-2H-isoindol-2-yl)ethyl]-1H-indole-5-methanesulphonamide A mixture of 2-(4,4-diethoxybutyl)-1H-isoindole-1,3(2H)-dione (0.58 g), the product of stage (b) (0.51 g) and 50% aqueous acetic acid (20 ml) was warmed to give a yellow solution which was then boiled in an atmosphere of nitrogen for 2 h. The mixture was cooled and extracted with ethyl acetate (5×25 ml). The extracts were washed with water (3×30 ml), dried ($Na_2SO_4$) and concentrated to a gum which on trituration with ether gave a cream solid (0.57 g). This was chromatographed elutine with ethyl acetate to give the product as a gum which solidified on trituration with ether. This material (0.29 g) was absorbed from acetone onto a PLC plate (Merck Kieselgel 60 F254, 20×20 cm) and eluted twice with ethyl acetate-cyclohexane (1:1). The pure indole was isolated from the stationary phase by Soxhlet extraction with ether for a day. Removal of the solvent gave a gum which on trituration with ethyl acetate gave the title compound as a cream solid, m.p. 186°–188° (32 mg).

(d) 3-(2-Aminoethyl)-1H-indole-5-methanesulphonamide, hydrochloride.

The product of stage (c) (0.3 g) was taken up in a solution of methylamine in ethanol (38%, 8 ml) to give a clear yellow solution which was kept at room temperature for 3 h. Solvent was removed in vacuo and the residual gum was re-evaporated with ethanol (2×8 ml), then taken up in methanol (5 ml) and filtered. The filtrate was treated with ethereal hydrogen chloride and diluted with ethyl acetate (50 ml). A gummy solid separated which was absorbed from methanol onto a PLC plate (Merck Kieselgel 60, 20×20 cm) and eluted in ethyl acetate-isopropanol-water-0.88 ammonia (25:15:8:2). The sulphonamide was extracted from the stationery phase with methanol (6×10 ml). The methanol solution was filtered and concentrated to a gum. This was taken up into ethyl acetate and filtered to remove silica and then treated with ethereal hydrogen chloride. The title compound separated as a cream solid (25 mg), m.p. 237°–239° (dec.).

Analysis Found: C, 45.5; H, 5.6; N, 13.5. $C_{11}H_{15}N_3O_2S.HCl$ requires C 45.6; H, 5.6; N, 14.5%.

T.l.c. (L) Rf 0.37.

Example 18

3-(2-Aminoethyl)-1H-indole-5-methanesulphonamide, maleate (a) Phenylmethyl[2-[5-[(aminosulphonyl)methyl]-1H-indol-3-yl]ethyl]carbamate A solution of the product of example 17 (c) (1.38 g) and hydrazine hydrate (0.72 ml) in ethanol (80 ml) and ethyl acetate (20 ml) was heated at reflux for 2 h. The mixture was cooled to room temperature and the resulting yellow solid filtered off. The filtrate was washed with saturated potassium carbonate (2×30 ml), the solvent evaporated and the crude free base which was identical with the product of example 17(d) was used in the next step without further purification.

A suspension of the base in dilute sodium carbonate (2N; 50 ml) was treated with benzyl chloroformate (1 ml) and stirred at room temperature for 1 h. The resulting suspension was extracted with ethyl acetate (4×30 ml), the organic layer dried ($MgSO_4$), solvent evaporated and the crude product, a black oil, (1.7 g) was purified by column chromatography (M) to give an oil (0.6 g). Crystallisation from chloroform (40 ml) gave the title compound as a white solid (0.4 g) m.p. 74°–75°.

(b) 3-(2-Aminoethyl)-1H-indole-5-methanesulphonamide, maleate

The product of stage (a) (0.14 g) was hydrogenated in methanol (10 ml) over prereduced 10% palladium oxide on carbon (0.08 g) until hydrogen uptake ceased. The catalyst was removed by filtration and the filtrate concentrated. The residue was purified by chromatography (F) to give the tryptamine as an oil (0.057 g) which was treated with maleic acid (0.026 g) in ethanol (5 ml) and methanol (1 ml). Solvent was evaporated and the residual oil crystallised from absolute ethanol (2 ml) to give the title compound as a light brown solid (0.03 g) m.p. 174°–175°.

Analysis Found: C, 48.6; H, 5.2; N, 10.7. $C_{11}H_{15}N_3O_2S.C_4H_4O_4$ requires C, 48.8; H, 5.2; N, 11.4%.

T.l.c. (L) Rf 0.37.

Example 19

3-[2-(Methylamino)ethyl]-1H-indole-5-methanesulphonamide, maleate (a) 4-[2-(3-Cyanopropylidene)hydrazino]benzenemethanesulphonamide A thick suspension of the product of example 17(b) (0.32 g) in water (2 ml) was stirred at room temperature and a solution of 3-cyanopropanal dimethyl acetal (0.26 g) in methanol (1 ml) was added followed by addition of hydrochloric acid (2N; 5 drops). Stirring was continued for 3 h. The resulting off-white solid was filtered off and dried in vacuo at 20° to give the title compound (0.31 g), m.p. 175°–176°.

(b) 3-(Cyanomethyl)-1H-indole-5-methanesulphonamide

A suspension of the product of stage (a) (3.1 g) and polyphosphate ester (30 g) in chloroform (60 ml) was heated at reflux for 10 min then poured onto ice and extracted with chloroform (4×20 ml). The combined organic extracts were dried, the solvent evaporated and the resulting oil purified by chromatography (G) to give the title compound as a yellow solid (0.32 g), m.p. 184°–185°.

(c) 3-[2-(Methylamino)ethyl]-1H-indole-5-methanesulphonamide, maleate

A solution of the product of stage (b) (0.21 g) in ethanolic methylamine (20 ml; 30% w/w) was hydrogenated over pre-reduced 10% palladium oxide on charcoal (0.4 g) (as a 50% aqueous paste) in ethanol (10 ml) at room temperature and atmospheric pressure for 3 h. The catalyst was removed by filtration (Hyflo) and the filtrate concentrated to an oil.

Chromatography (N) and (O) gave the free base as a white solid (0.18 g). This was dissolved in hot ethanol (10 ml) and a solution of maleic acid (0.1 g) in ethanol (3 ml) was added.

Ether (10 ml) was added until a cloudy solution resulted. On cooling the title compound deposited as a cream powder (75 mg), m.p. 153°–154°.

Analysis Found: C, 50.0; H, 5.4; N, 10.8. $C_{12}H_{17}N_3O_2S.C_4H_4O_4$ requires C, 50.4; H, 5.0; N, 11.0%.

T.l.c. (O) Rf 0.27.

Example 20

3-[2-(Ethylamino)ethyl]-1H-indole-5-methanesulphonamide, hydrochloride, hemihydrate, compound with ethanol (5:5:2.5:1)

A solution of the product of example 19(b) (0.32 g) in ethanolic ethylamine (30 ml; 33% w/w) was hydrogenated over pre-reduced 10% palladium oxide on charcoal (0.4 g, 50% aqueous paste) in ethanol (10 ml) at room temperature and atmospheric pressure overnight. The catalyst was removed by filtration (Hyflo) and the filtrate concentrated to an oil (0.30 g). Chromatography (O) gave the free base as a foam (0.28 g). A solution of the tryptamine (0.28 g) in absolute ethanol (10 ml) and methanol (10 ml) was treated with ethanolic hydrogen chloride (ice cooling) to pH 1, ether (20 ml) was added and the resulting suspension was left in the fridge overnight. The title compound was filtered off as a white powder (0.24 g) m.p. 143°–144°.

Analysis Found: C, 48.1; H, 6.3; N, 12.4. $C_{13}H_{19}N_3O_2S.HCl.0.5H_20.0.2C_2H_6O$ requires C, 47.9; H, 6.7; N, 12.5%.

T.l.c. (O) Rf 0.48.

Example 21

3-[2-(Dimethylamino)ethyl]-1H-indole-5-methanesulphonamide, hydrochloride, compound with isopropanol (10:10:1.5)

A solution of the product of example 19(b) (0.2 g) in methanolic dimethylamine (1:1, 20 ml) was hydrogenated over pre-reduced 10% palladium oxide on charcoal (0.4 g, 50% aqueous paste) in methanol (10 ml) at room temperature and atmospheric pressure for 5 h. The catalyst was removed by filtration (hyflo) and the filtrate was concentrated to an oil. Chromatography (B) gave the tryptamine as a white foam (0.16 g). Ethanolic hydrogen chloride was added dropwise to a cold solution (ice bath) of the free base in isopropanol (4 ml) (until pH 4) and the title compound was precipitated as a white powder (0.14 g) m.p. 237°–239°.

Analysis Found: C, 49.1; H, 6.5; N, 12.6. $C_{13}H_{19}N_3O_2S.HCl.0.15C_3H_8O$ requires C, 49.4; H, 6.5; N, 12.9%.

T.l.c. (B) Rf 0.23.

Example 22

N-Methyl-3-[2-(methylamino)ethyl]-1H-indole-5-methanesulphonamide, compound with maleic acid and ethanol (10:10:1)

A solution of the product of example 2(b) (0.9 g) in dry tetrahydrofuran (20 ml) was added to a suspension of lithium aluminium hydride (0.9 g) in dry tetrahydrofuran (100 ml) and heated for 2 h at reflux. The resulting suspension was cooled, treated with a saturated solution of potassium carbonate (ice cooling), extracted with methanol (3×25 ml) and the extract concentrated. The residual oil was purified by column chromatography (K) to give the tryptamine as an oil (0.37 g). This was dissolved in absolute ethanol (5 ml) and treated with ethanolic maleic acid (0.5M; 2.6 ml). A sticky precipitate separated. Methanol was added dropwise until a clear solution resulted which was then concentrated under reduced pressure to approx. 1 ml and the title compound crystallised as an off-white solid (0.2 g) m.p. 123°–124°.

Analysis Found: C, 51.0; H, 5.8; N, 10.1. $C_{13}H_{19}N_3O_2S.C_4H_4O_4.0.1C_2H_6O$ requires C, 51.4; H, 5.9; N, 10.45%.

T.l.c. (K) Rf 0.32.

Example 23

N-Methyl-3-[2-(methylamino)ethyl]-1H-indole-5-methanesulphonamide (a) 3-(2-Chloroethyl)-N-methyl-1H-indole-5-methanesulphonamide A solution of the product of example 6(a) (0.25 g) in chloroform (3 ml) was added to a solution of polyphosphate ester (2.5 g) in chloroform (2 ml) and the solution was heated under reflux with stirring for 5 min. The solution became dark yellow. It was then cooled and poured onto ice (20 g) and chloroform (5 ml) and stirred. The aqueous phase was brought to pH 8 by the addition of sodium bicarbonate and the organic layer was collected. The aqueous layer was extracted with chloroform (4×20 ml) and the extracts dried ($Na_2SO_4$). Removal of the solvent in vacuo gave the crude 3-chloroethyl indole as a light brown viscous oil (0.677 g) which was used in the next experiment without further purification.

T.l.c. (P) Rf 0.58 (major), Rf 0.64 (minor).

(b) N-Methyl-3-[2-(methylamino)ethyl]-1H-indole-5-methanesulphonamide

The Product of stage (a) (0.677 g) was taken up in 33% methylamine in ethanol (25 ml) and heated in a steel autoclave at 80°–90° for 16 h. The dark yellow solution was concentrated to a light brown oil (1.25 g) which was chromatographed (J) to give the title compound (0.039 g) as a light yellow glass which was shown by n.m.r. and t.l.c. (L) Rf 0.4 to be identical with the product of Example 22.

Example 24

3-(2-Aminoethyl)-1H-indole-5-methanesulphonamide hemisuccinate

A mixture of the product from Example 17 stage (b) (10.0 g) and 4-chlorobutanal dimethyl acetal (6.23 g) in ethanol (260 ml) and water (53 ml) was stirred at 50° for 1.5 h. Ammonium acetate (8.69 g) was then added and the resultant milk was heated to reflux and stirred for 3.5 h. The mixture was then cooled and reduced in volume in vacuo to ca. 30 ml. The orange residue was partitioned between 5N potassium carbonate (800 ml) and ethyl acetate (3×500 ml). The combined organic extracts were then washed with 5N potassium carbonate (200 ml) and water (200 ml). The organic solution was then dried ($Na_2SO_4$) and concentrated in vacuo. The residual brown oil was chromatographed (J) to give a brown oil which slowly crystallised (2.12 g).

A portion of this material (1.0 g) was dissolved in boiling ethanol (25 ml), and added to a hot solution of succinic acid (0.22 g) in ethanol (15 ml). The solid that crystallised on cooling was filtered off, washed with ethanol (3×10 ml) and dried in vacuo at 35° for 6 h to give the title sulphonamide as fawn microcrystals (1.18 g), m.p. 230°–231.5° (foams). This product was shown by n.m.r. and t.l.c. (J, Rf 0.17) to be identical with the product from Example 17(d).

Example 25

3-[2-(Methylamino)ethyl]-N-methyl-1H-indole-5-methanesulphonamide, maleate quarter hydrate (a) 3-[2-(Formylamino)ethyl]-N-methyl-1H-indole-5-methanesulphonamide A mixture of the product of example 1(c) as the free base (0.534 g) and N-formyl imidazole (0.211 g) was stirred in dry tetrahydrofuran (30 ml) for 30 min. After removal of the solvent by evaporation under reduced pressure, the residue was partitioned between chloroform (50 ml) and 2N hydrochloric acid (50 ml). The aqueous phase was basified using 2N sodium hydroxide (pH 9) and was extracted with ethyl acetate (2×50 ml). The combined organic extracts were dried ($Na_2SO_4$) and evaporated under reduced pressure yielding a pale yellow gum. This was chromatographed (J) to give the title compound as a colourless gum (0.35 g).

T.l.c. (J) Rf 0.81.

(b) 3-[2-(Methylamino)ethyl]-N-methyl-1H-indole-5-methanesulphonamide, maleate, quarter hydrate To a stirred suspension of lithium aluminium hydride (0.77 g) in dry tetrahydrofuran (5 ml) in a stream of nitrogen was added a solution of the product of stage (a) (0.3 g) in dry tetrahydrofuran (10 ml). The suspension was heated under reflux for 5 h. Water (1 ml) in tetrahydrofuran (9 ml) was added to the ice cold mixture and the suspension was filtered through a pad of "hyflo". Evaporation of the filtrate gave a pale yellow gum which was chromatographed (J) to give the tryptamine as a colourless gum (0.15 g). This was dissolved in hot 2-propanol (2 ml) and a solution of maleic acid (0.062 g) in ethanol (1 ml) was added. On cooling the title compound deposited as an off-white powder (0.18 g), m.p. 122°–124°, identical with the product of example 22.

Example 26

3-[2-(Ethylamino)ethyl]-N-methyl-1H-indole-5-methanesulphonamide compound with creatinine and sulphuric acid (1:1:1)

A mixture of the product of example 7 (0.2 g) and acetaldehyde (0.044 g) was stirred in methanol (10 ml) for 15 min. To the pale yellow solution was added sodium cyanoborohydride (0.062 g) and the mixture was stirred at room temperature for 1 h. 2N Hydrochloric acid (2 ml) was added and the volume of the solution was reduced to about 2 ml by evaporation under reduced pressure. Water (20 ml) was added and the solution was washed with ethyl acetate (25 ml). The phases were separated, potassium carbonate (5 g) was added to the aqueous phase which was then extracted with ethyl acetate (2×25 ml). Evaporation of the dried ($Na_2SO_4$) combined organic extracts gave a pale yellow gum which was chromatographed (J) to give the product as a colourless gum (0.08 g). This was dissolved in ethanol (4 ml) containing water (0.5 ml) and an aqueous solution of creatinine and sulphuric acid (1:1, 2M, 0.14 ml) was added. On cooling the title compound deposited as a white powder (0.089 g), m.p. 197°–198°.

Analysis Found: C, 42.6; H,5.9; N, 16.5. $C_{14}H_{21}N_3O_2S.C_4H_7N_3O.H_2SO_4$ requires C, 42.7; H,6.0; N, 16.6%.

T.l.c. (J) Rf 0.37.

Example 27

3-(3-Aminopropyl)-N-methyl-1H-indole-5-methanesulphonamide, compound with hydrogen chloride, water and ether (100:100:85:11)

(a) 2-(5,5-Dimethoxypentyl)-1H-isoindole-1,3(2H)-dione

A mixture of potassium phthalimide (0.48 g) and 5-bromopentanal dimethyl acetal (0.50 g) in dry dimethylformamide (3 ml) was stirred at 90° for 5 h and then allowed to cool. The resultant yellow suspension was then partitioned between water (30 ml) and ethyl acetate (3×30 ml). The combined organic extracts were then dried ($Na_2SO_4$) and concentrated in vauco.

The residual pale yellow oil was purified by flash chromatography (Kieselgel 9385, ether) to give the title compound as a white solid (0.33 g), m.p. 34.5°–37°.

(b) 3-[3-(1,3-Dihydro-1,3-dioxo-2H-isoindol-2-yl)propyl]-N-methyl-1H-indole-5-methanesulphonamide A suspension of the product from stage (a) (2.55 g) and the product from Example 1(b) (2.50 g) in 10% aqueous acetic acid (200 ml) was stirred at room temperature for ½ h and then at reflux for 1¼ h. The yellow gummy suspension was allowed to cool and was then extracted with ethyl acetate (3×200 ml), dried ($Na_2SO_4$) and concentrated in vacuo to give an orange foam (3.59 g). This material was used in stage (C). A portion of this foam (0.50 g) was chromatographed (G) to give the impure title sulphonamide as an orange foam which failed to crystallised from common organic solvents (0.14 g), m.p. 58°–66°.

T.l.c. Rf 0.37 (Q).

(c) 3-(3-Aminopropyl)-N-methyl-1H-indole-5-methanesulphonamide, compound with hydrogen chloride, water and ether (100:100:85:11)

Hydrazine hydrate (3.0 ml) was added to a stirred, refluxing suspension of the product from stage (b) (2.90 g) in ethanol (90 ml) and stirring was continued for 3 h. The cooled yellow suspension was evaporated in vacuo and the residual yellow solid was partitioned between 2N sodium bicarbonate (150 ml) and ethyl acetate (3×150 ml). The combined organic solutions were then dried ($Na_2SO_4$) and evaporated in vacuo.

The residual yellow foam (1.06 g) was chromatographed (J) to give an orange gum (0.45 g).

A portion of this gum (0.39 g) was dissolved in absolute ethanol (5 ml) and ethanolic hydrogen chloride (1 ml) was added. The stirred solution was diluted with dry ether (ca 80 ml) and the precipitated solid was filtered off, washed with dry ether (4×15 ml) and dried.

The solid was reprecipitated three times from absolute ethanol (ca 15 ml) to give the title salt as a hygroscopic brown solid (0.085 g) m.p. 212°–215° which slowly turned to a gum.

T.l.c.. (J) Rf 0.2.

Analysis Found: C, 47.8; H, 6.7; N, 12.3. $C_{13}H_{19}N_3O_2S.HCl.0.85H_2O.0.11C_4H_{10}O$ requires C, 47.3; H, 6.7; N, 12.3%.

Example 28

Phenylmethyl [2-[5-[[(methylamino)sulphonyl]methyl]-1H-indol-3-yl]ethyl]carbamate Sodium hydride (80% in oil, 13 mg) was added to a stirred, ice cooled solution of the product from Example 18 stage (a) (150 mg) in dry dimethylformamide (3 ml) under nitrogen. The suspension was stirred at room temperature for ½ h and then cooled in ice. Methyl iodide (0.03 ml) was added and the solution stirred at room temperature for 7 h with further methyl iodide (0.03 ml) added after 3 h. The solution was partitioned between water (30 ml) and ethyl acetate (4×20 ml). The combined organic extracts were then washed with water (4×20 ml), dried ($Na_2SO_4$) and concentrated in vacuo. The residual brown oil (140 mg) was chromatographed (E) to give the title carbamate as a brown oil (16 mg). This product was shown by n.m.r. and t.l.c. (E, Rf 0.35) to be identical with the product of Example 2(b).

Example 29

3-(2-Aminoethyl)-N-methyl-1H-indole-5-methanesulphonamide (Method G)

To a solution of the product of example 5(b) (0.1 g) and cobaltous chloride hexahydrate (0.19 g) in ethanol (5 ml) was added sodium borohydride (0.15 g) and the resulting suspension was heated at reflux for 1 h. It was poured into dilute hydrochloric acid (2N, 10 ml). T.l.c. (F) showed the solution contained a component Rf 0.26 identical with that of a sample of the product of Example 1(c).

Example 30

N-Methyl-3-[2-(phenylmethylideneamino)ethyl]-1H-indole-5-methanesulphonamide compound with water and ether (4:1:1)

A mixture of the product of example 1(c) as the free base (0.536 g) benzaldehyde (0.232 g) and 3 Å molecular sieves (3 g) in ethanol (20 ml) was boiled under reflux for 3 h. The solution was then stirred at room temperature for 1 h and filtered through hyflo. The filtrate was concentrated and the residue triturated under ether (25 ml) to give the title compound as an off-white powder (0.6 g), m.p. 130°–132°.

Analysis Found: C, 63.4; H, 6.0; N, 11.1. $C_{19}H_{21}N_3O_2S.0.25H_2O.0.25C_4H_{10}O$ requires C, 63.5; H, 6.4; N, 11.1%.

PHARMACEUTICAL EXAMPLES

Tablets

These may be prepared by the normal methods such as wet granulation or direct compression.

| A. Direct Compression | |
|---|---|
| | mg/tablet |
| Active ingredient | 10.0 |
| Microcrystalline Cellulose USP | 188.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the compression weight and using punches to suit.

| B. Wet Granulation | |
|---|---|
| | mg/tablet |
| Active ingredient | 10.0 |
| Lactose BP | 143.5 |
| Starch BP | 30.0 |
| Pregelatinised Maize Starch BP | 15.0 |
| Magnesium Stearate BP | 1.5 |
| Compression weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

| C. For Buccal Administration | |
|---|---|
| | mg/tablet |
| Active ingredient | 10.0 |
| Lactose BP | 86.8 |
| Sucrose BP | 86.7 |
| Hydroxypropyl methylcellulose | 15.0 |
| Magnesium Stearate BP | 1.5 |
| Compression weight | 200.0 |

The active ingredient is sieved through a suitable sieve and blended with the lactose, sucrose and hydroxypropylmethylcellulose. Suitable volumes of purified water are added and the powders are granulated. After drying, the granules are screened and blended with the magnesium stearate. The granules are then compressed into tablets using suitable punches.

The tablets may be film-coated with suitable film-forming materials, such as hydroxypropyl methylcellulose, using standard techniques. Alternatively the tablets may be sugar coated.

| Capsules | |
|---|---|
| | mg/capsule |
| Active ingredient | 10.0 |
| *Starch 1500 | 89.0 |
| Magnesium Stearate BP | 1.0 |
| Fill Weight | 100.0 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| Syrup | |
|---|---|
| | mg/5 ml dose |
| Active ingredient | 10.0 |
| Sucrose BP | 2750.0 |
| Glycerine BP | 500.0 |
| Buffer | |
| Flavour | |
| Colour | as required |
| Preservative | |
| Distilled water to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup produced is clarified by filtration.

| Suppositories | |
| --- | --- |
| Active ingredient | 10.0 mg |
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository moulds.

| Injection for Intravenous Administration | |
| --- | --- |
| | % w/v |
| Active ingredient | 0.2 |
| Sodium Chloride BP | as required |
| Water for Injection BP to | 100.00 |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed uner an inert atmosphere of nitrogen or other suitable gas.

| Inhalation Cartridges | |
| --- | --- |
| | mg/cartridge |
| Active ingredient micronised | 1.0 |
| Lactose BP | 39.0 |

The active ingredient is micronised (Microniser is a Registered Trade Mark) in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler (Registered Trade Mark).

| Metered Dose Pressurised Aerosol | | |
| --- | --- | --- |
| | mg/metered dose | per can |
| Active ingredient micronised | 0.500 | 120.0 mg |
| Oleic Acid BP | 0.050 | 12.0 mg |
| Trichlorofluoromethane BP | 22.250 | 5.34 mg |
| Dichlorofluoromethane BP | 62.2 | 14.92 g |

The active ingredient is micronised in a fluid energy mill to a fine particle size range. The oleic acid is mixed with the trichlorofluoromethane at a temperature of 10°–15° C. and the pulverized drug is mixed into the solution with a high shear mixer. The suspension is metered into aluminium aerosol cans and suitable metering valves, delivering a metered amount of 85 mg of suspension, are crimped onto the cans and the dichlorodifluoromethane is pressure filled into the cans through the valves.

In the above examples, the active ingredient is preferably 3-(2-aminoethyl)-N-methyl-1H-indole-5-methanesulphonamide which may be in the form of a physiologically acceptable salt, for example, the hydrochloride or succinate salt.

We claim:

1. A compound of formula (I):

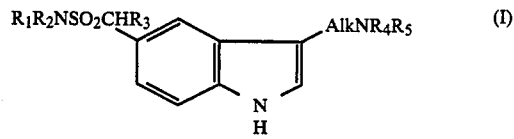

wherein $R_1$ represents a hydrogen atom or a $C_{1-6}$ alkyl or $C_{3-6}$ alkenyl group;

$R_2$ represents a hydrogen atom or a $C_{1-3}$ alkyl, $C_{3-6}$ alkenyl, phenyl, phen($C_{1-4}$)alkyl or $C_{5-7}$ cycloalkyl group;

$R_3$ represents a hydrogen atom or a $C_{1-3}$ alkyl group;

$R_4$ and $R_5$, which are the same or different, each represents a hydrogen atom or a $C_{1-3}$ alkyl or propenyl group or $R_4$ and $R_5$ together form a benzylidene group; and Alk represents an alkylene chain containing two or three carbon atoms which is unsubstituted or substituted by not more than two $C_{1-3}$ alkyl groups, and physiologically acceptable salts and solvates thereof.

2. A compound according to claim 1, wherein, in the formula (I), $R_1$ represents a hydrogen atom or a $C_{1-6}$ alkyl group and $R_2$ represents a hydrogen atom or a $C_{1-3}$ alkyl, $C_{3-6}$ alkenyl or phen($C_{1-4}$) alkyl group.

3. A compound according to claim 1, wherein in the formula (I), $R_3$ represents a hydrogen atom.

4. A compound according to claim 1, wherein in the formula (I), $R_4$ and $R_5$, which are the same or different, each represents a hydrogen atom or a $C_{1-3}$ alkyl group.

5. A compound of the formula (I)

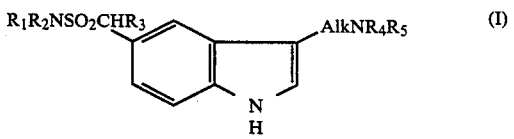

wherein $R_1$ represents a hydrogen atom or a $C_{1-3}$ alkyl group;

$R_2$ represents a hydrogen atom or a $C_{1-3}$ alkyl group, a $C_{3-4}$ alkenyl group or a phen($C_{1-2}$)alkyl group;

$R_3$ represents a hydrogen atom;

$R_4$ and $R_5$, which are the same or different, each represents a hydrogen atom or a $C_{1-3}$ alkyl group; and Alk represents an alkylene chain containing two or three carbon atoms which is unsubstituted or substituted by not more than two $C_{1-3}$ alkyl groups, and physiologically acceptable salts and solvates thereof.

6. A compound according to claim 5, wherein in the formula (I):

$R_1$ represents a hydrogen atom or a methyl group;

$R_2$ represents a hydrogen atom or a methyl, ethyl, isopropyl, propenyl or benzyl group;

$R_3$ represents a hydrogen atom; and $R_4$ and $R_5$ which may be the same or different, each represents a hydrogen atom or a methyl group.

7. A compound according to claim 6, wherein in the formula (I) Alk represents an unsubstituted alkylene chain containing two or three carbon atoms.

8. A compound according to claim 5, wherein the physiologically acceptable salt is a hydrochloride, hydrobromide, sulphate, fumarate, maleate or succinate.

9. A compound according to claim 8, wherein the physiologically acceptable salt is a succinate.

10. A compound according to claim 5, wherein, in the formula (I), $R_1$ represents a hydrogen atom or a $C_{1-3}$ alkyl group; $R_2$ represents a $C_{1-3}$ alkyl group or a $C_{3-4}$ alkenyl group; $R_3$ and $R_4$ each represents a hydrogen atom; and $R_5$ represents a hydrogen atom or a $C_{1-3}$ alkyl group.

11. A compound according to claim 1 which is 3-(2-(methylamino)ethyl)-N-methyl-1H-indole-5-methanesulphonamide; 3-(2-aminoethyl)-N,N-dimethyl-1H-indole-5-methanesulphonamide; 3-(2-aminoethyl)-N-(2-propenyl)-1H-indole-5-methanesulphonamide; or a physiologically acceptable salt or solvate thereof.

12. 3-(2-Aminoethyl)-N-methyl-1H-indole-5-methanesulphonamide or a physiologically acceptable salt or solvate thereof.

13. A compound according to claim 1 wherein the physiologically acceptable salt is a hydrochloride, hydrobromide, sulphate, fumarate, maleate or succinate.

14. 3-(2-Aminoethyl)-N-methyl-1H-indole-5-methanesulphonamide, hydrochloride; or 3-(2-aminoethyl)-N-methyl-1H-indole-5-methanesulphonamide, succinate.

15. A pharmaceutical composition for use in the treatment of migraine comprising an effective amount of at least one compound of formula (I) as defined in claim 1 or a physiologically acceptable salt or solvate thereof together with one or more physiologically acceptable carriers or excipients.

16. A method of treating a patient suffering from migraine which comprises administering to the patient an effective amount of a compound of formula (I) as defined in claim 1 or a physiologically acceptable salt or solvate thereof.

17. A pharmaceutical composition for use in the treatment of migraine comprising an effective amount of at least one compound of formula (I) as defined in claim 5 or a physiologically acceptable salt or solvate thereof together with one or more physiologically acceptable carriers or excipients.

18. A method of treating a patient suffering from migraine which comprises administering to the patient an effective amount of a compound of formula (I) as defined in claim 5 or a physiologically acceptable salt or solvate thereof.

* * * * *

UNITED STATES PATENT AND TRADEMARK OFFICE

CERTIFICATE EXTENDING PATENT TERM
UNDER 35 U.S.C. § 156

PATENT NO.: 4,816,470

DATED: March 28, 1989

INVENTORS: Michael D. Dowle et al.

PATENT OWNER: Glaxo Group Limited

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

275 DAYS with all rights pertaining thereto as provided by 35 U.S.C. § 156(b).

I have caused the seal of the Patent and Trademark Office to be affixed this 20th day of September 1994.

Bruce A. Lehman
Assistant Secretary of Commerce and
  Commissioner of Patents and Trademarks